(12) United States Patent
Birnkrant et al.

(10) Patent No.: US 9,386,914 B2
(45) Date of Patent: Jul. 12, 2016

(54) VIDEO ENDOSCOPIC DEVICE WITH DETACHABLE CONTROL CIRCUIT

(75) Inventors: Dashiell Birnkrant, Worcester, MA (US); James P. Barry, Charlton, MA (US)

(73) Assignee: Karl Storz Endovision, Inc., Charlton, MA (US)

( * ) Notice: Subject to any disclaimer, the term of this patent is extended or adjusted under 35 U.S.C. 154(b) by 1394 days.

(21) Appl. No.: 12/038,066

(22) Filed: Feb. 27, 2008

(65) Prior Publication Data

US 2008/0249355 A1     Oct. 9, 2008

Related U.S. Application Data

(63) Continuation-in-part of application No. 11/696,524, filed on Apr. 4, 2007, now Pat. No. 8,029,440.

(51) Int. Cl.
*A61B 1/06* (2006.01)
*A61B 1/267* (2006.01)
*A61B 1/00* (2006.01)
(Continued)

(52) U.S. Cl.
CPC ............. *A61B 1/267* (2013.01); *A61B 1/00105* (2013.01); *A61B 1/0684* (2013.01); *A61B 1/00016* (2013.01); *A61B 1/0052* (2013.01); *G02B 23/2476* (2013.01)

(58) Field of Classification Search
CPC .... A61B 1/0638; A61B 5/0084; A61B 1/018; A61B 1/267; A61B 1/00101; A61B 1/0014
USPC ......... 600/160, 187, 188, 196, 190, 120, 112, 600/169, 178, 185, 109, 117, 104, 323, 139, 600/300, 153, 106, 125, 131, 394, 193, 141, 600/197, 199, 200; 348/65, 49; 128/200.26; 382/131; 606/1, 46; 604/533, 210, 263
See application file for complete search history.

(56) References Cited

U.S. PATENT DOCUMENTS 3,978,850 A  *  9/1976  Moore et al. .................. 600/200
4,279,246 A      7/1981  Chikama
4,807,594 A      2/1989  Chatenever
(Continued)

FOREIGN PATENT DOCUMENTS

EP          1847214 A2    10/2007
JP         11123175 A      5/1999
(Continued)

OTHER PUBLICATIONS

Canadian Office Action; Canadian Application No. 2,627,127; Aug. 6, 2010; 5 pages.
(Continued)

*Primary Examiner* — Anhtuan T Nguyen
*Assistant Examiner* — Jae Woo
(74) *Attorney, Agent, or Firm* — Whitmyer IP Group LLC

(57) ABSTRACT

An endoscopic device including a control circuit that is detachably connectable to a handle, where the control circuit functions and is compatible with a wide variety of displays. The handle of the endoscopic device is provided with a connector to transmit image data from a distal end to the detachable control circuit. The control circuit may be provided with a keyed outer surface to guide and maintain the control circuit in an engaged position relative to the handle and connector.

23 Claims, 14 Drawing Sheets

(51) Int. Cl.
*A61B 1/005* (2006.01)
*G02B 23/24* (2006.01)

(56) References Cited

U.S. PATENT DOCUMENTS

| | | | | |
|---|---|---|---|---|
| 5,647,840 | A | 7/1997 | D'Amelio et al. | |
| 5,800,344 | A * | 9/1998 | Wood et al. | 600/188 |
| 5,841,149 | A * | 11/1998 | Spink et al. | 250/559.29 |
| 6,013,081 | A * | 1/2000 | Burkinshaw et al. | 606/88 |
| 6,083,151 | A * | 7/2000 | Renner et al. | 600/114 |
| 6,095,661 | A * | 8/2000 | Lebens et al. | 362/184 |
| 6,106,457 | A * | 8/2000 | Perkins et al. | 600/175 |
| 6,296,528 | B1 * | 10/2001 | Roberts et al. | 439/676 |
| 6,386,452 | B1 | 5/2002 | Kawamura | |
| 6,413,209 | B1 * | 7/2002 | Thompson | 600/169 |
| 6,494,826 | B1 * | 12/2002 | Chatenever et al. | 600/112 |
| 6,543,447 | B2 | 4/2003 | Pacey | 128/200.26 |
| 6,655,377 | B2 | 12/2003 | Pacey | 128/200.26 |
| 6,676,598 | B2 * | 1/2004 | Rudischhauser et al. | 600/188 |
| 6,840,903 | B2 | 1/2005 | Mazzei et al. | |
| 6,875,169 | B2 * | 4/2005 | Berci et al. | 600/112 |
| 6,929,600 | B2 * | 8/2005 | Hill | 600/120 |
| 7,048,686 | B2 * | 5/2006 | Kameya et al. | 600/179 |
| 7,066,903 | B2 * | 6/2006 | Yarger | 604/35 |
| 7,280,853 | B2 * | 10/2007 | Hassan et al. | 455/574 |
| 7,776,004 | B2 * | 8/2010 | Yarger | 604/35 |
| 7,794,421 | B2 * | 9/2010 | Yarger | 604/35 |
| 7,828,723 | B2 * | 11/2010 | Ueno et al. | 600/136 |
| 7,942,810 | B2 * | 5/2011 | Uchimura et al. | 600/117 |
| 7,946,981 | B1 * | 5/2011 | Cubb | 600/194 |
| 8,029,440 | B2 * | 10/2011 | Birnkrant et al. | 600/188 |
| 2002/0022763 | A1 * | 2/2002 | Sano et al. | 600/109 |
| 2002/0022769 | A1 * | 2/2002 | Smith et al. | 600/188 |
| 2003/0004397 | A1 * | 1/2003 | Kameya et al. | 600/101 |
| 2003/0088156 | A1 * | 5/2003 | Berci et al. | 600/188 |
| 2003/0195390 | A1 * | 10/2003 | Graumann | 600/188 |
| 2003/0220611 | A1 * | 11/2003 | Yarger | 604/122 |
| 2004/0133073 | A1 * | 7/2004 | Berci et al. | 600/112 |
| 2005/0054974 | A1 * | 3/2005 | Yarger | 604/35 |
| 2005/0148364 | A1 * | 7/2005 | Yamashita | 455/557 |
| 2005/0148821 | A1 * | 7/2005 | Berci et al. | 600/188 |
| 2005/0192481 | A1 * | 9/2005 | Berci et al. | 600/188 |
| 2005/0244801 | A1 * | 11/2005 | DeSalvo | 434/262 |
| 2005/0279355 | A1 * | 12/2005 | Loubser | 128/200.26 |
| 2006/0004260 | A1 * | 1/2006 | Boedeker et al. | 600/188 |
| 2006/0020171 | A1 * | 1/2006 | Gilreath | 600/188 |
| 2006/0058584 | A1 * | 3/2006 | Hirata | 600/179 |
| 2006/0069314 | A1 * | 3/2006 | Farr | 600/179 |
| 2006/0095007 | A1 * | 5/2006 | Yarger | 604/129 |
| 2006/0287576 | A1 * | 12/2006 | Tsuji et al. | 600/132 |
| 2006/0293562 | A1 * | 12/2006 | Uchimura et al. | 600/110 |
| 2007/0106121 | A1 * | 5/2007 | Yokota et al. | 600/188 |
| 2007/0173697 | A1 * | 7/2007 | Dutcher et al. | 600/188 |
| 2007/0175482 | A1 * | 8/2007 | Kimmel et al. | 128/207.14 |
| 2007/0195539 | A1 * | 8/2007 | Birnkrant | 362/458 |
| 2007/0197873 | A1 * | 8/2007 | Birnkrant | 600/160 |
| 2007/0203449 | A1 * | 8/2007 | Yarger | 604/35 |
| 2007/0230167 | A1 * | 10/2007 | McMahon et al. | 362/157 |
| 2008/0039693 | A1 * | 2/2008 | Karasawa | 600/175 |
| 2008/0200766 | A1 * | 8/2008 | Ayoun et al. | 600/199 |
| 2008/0249355 | A1 * | 10/2008 | Birnkrant et al. | 600/112 |
| 2008/0249370 | A1 * | 10/2008 | Birnkrant et al. | 600/188 |

FOREIGN PATENT DOCUMENTS

| | | |
|---|---|---|
| JP | 2003036708 A | 2/2003 |
| JP | 2004309719 A | 11/2004 |
| JP | 3108837 U | 4/2005 |
| WO | 9846121 A1 | 10/1998 |
| WO | 2004035106 A2 | 4/2004 |

OTHER PUBLICATIONS http://www.mercksource.com/pp/us/cns/cns_hl_dorlands_spl it.jsp?pg=/ppdocs/us/common/doriands/doriand/two/OOOO16045.htm , Nov. 4, 2009.
Partial European Search Report, EP08006215, Jul. 25, 2008, 2 pages.

* cited by examiner

VIDEO ENDOSCOPIC DEVICE WITH DETACHABLE CONTROL CIRCUIT

CROSS-REFERENCE

The application is a continuation-in-part of U.S. patent application Ser. No. 11/696,524 filed Apr. 4, 2007.

FIELD OF THE INVENTION

The invention relates to an endoscope device, and more particularly to an endoscope device that may be used with many differing video monitors and signal formats.

BACKGROUND OF THE INVENTION

A number of medical procedures require the use of endoscopic devices. In one application, the endoscopic device comprises a laryngoscope that is used to intubate a patient. Ventilation may be provided to a patient through an endotracheal tube. This tube may be inserted into the trachea with the help of the laryngoscope. It should be noted that when the tube is inserted, the patient is asleep hyperoxygenated and then paralyzed for the procedure, and therefore not breathing. As the ventilator is not yet in operation, the physician must work quickly to insert the endotracheal tube. Any delay in this process is highly undesirable. Other applications for endoscopes include minimally invasive surgical techniques and difficult to access surgical areas.

With the advent of endoscopic equipment and small cameras, instrumentation can enable viewing of, for example, the cords and larynx on a video screen facilitating the intubation of the patient in a relatively quick and safe manner or the viewing of an area inside the body where a procedure is to be performed.

One problem that traditional video endoscopes face is the limited interface ability they have with different types of monitors. For example, a video endoscope typically is designed and can only be used with a single type of monitor, such as an O.R. monitor or a P.C. This is disadvantageous as the physician may desire to switch monitors, for example, the endoscope may be attached to an O.R. monitor but the physician wants to connect the endoscope to a relatively small portable computer monitor as a patient is transported. The endoscope would then have to be replaced with a device capable of functioning with a P.C. monitor.

Yet another problem associated with video endoscopes is the fact that, many image processing devices are permanently affixed to the device such that if the physician desired to have a different image processor, the physician must exchange the entire endoscope. This can cause delay in performing a particular procedure, which as previously stated, is highly undesirable.

Many differing types of surgical procedures are now commonly performed with the aid of either a direct view or video endoscope to remotely view an area where a procedure is to be performed. However, due to the fact that with currently know devices, the image processing circuitry is integrally formed with the endoscope and therefore, any change in the image processor requires a change of the entire endoscope. This means that during a procedure, the entire endoscope must be withdrawn from the surgical site and a new endoscope inserted, which is again, highly undesirable.

Another problem with current endoscopic devices, including endoscopes and laryngoscopes, is that they need to be sterilized after use. The image processing circuitry that is integrally formed in the endoscopic device can become damaged when exposed to very high temperatures such as are used for sterilization.

SUMMARY OF THE INVENTION

It is therefore desired to provide an endoscopic device that is capable of functioning with many differing monitors.

It is also desired to provide an endoscopic device that allows for the changing of the image processor quickly and easily.

It is further desired to provide an endoscopic device that allows for different image processors to be used in a single device.

It is further desired to provide an endoscopic device that is compatible with many differing signal formats.

These and other objectives are achieved by providing an endoscopic device having a detachable image processing device.

For example, in one embodiment, the endoscopic device is provided as a laryngoscope and includes a blade having a smooth upper surface so as not to interfere with the physician's direct visualization of the areas in and around the laryngopharynx during intubation. The laryngoscope is provided with a digital imaging chip and an illumination device, e.g. a Light Emitting Diode (LED) for illumination of an area to be viewed. It is contemplated that the digital imaging chip may comprise, for example, either a CCD, a C-Mos chip, or the like.

It is further contemplated that the endoscopic device may comprise a rigid or flexible video endoscope. Additionally, the digital imaging chip may be provided as a "hard-wired" or as a "wireless" device for transmitting image data picked up from the area to be viewed and may be positioned at either a distal end of the laryngoscope blade or endoscope shaft or in the handle.

In one advantageous embodiment, a digital imaging chip and an LED are positioned in the laryngoscope blade. The digital imaging chip and the LED may further be detachably connectable to the laryngoscope blade via, for example, an enclosure that may be detachably connectable to the laryngoscope blade. The enclosure may be provided with an elongated case and be provided with a coupling mechanism for coupling the enclosure to the handle and/or blade. In one embodiment, the imaging chip and the LED are provided at a distal end of the enclosure, while the coupling mechanism is provided at the opposite proximal end of the enclosure such that electrical connections may be provided for the imaging chip and the LED. In this manner, electrical power may be transmitted to the LED to illuminate the area ahead of the blade, while the digital imaging chip may generate and transmit image data back to imaging circuitry positioned in the handle. It is further provided that the LED may be provided as a relatively high-powered LED and is used to heat a window at the distal end of the enclosure such that the window is maintained free of fogging. The LED may be run, for example, at half power.

In addition, the enclosure may be positioned in a channel provided in the blade to securely hold the enclosure.

In another advantageous embodiment, a universal control circuit may be positioned in the handle of the laryngoscope. The universal control circuit may be removable and may include a connector to couple to the handle, or may include a connector that couples directly to the enclosure. The universal control circuit may include many differing configurations including, for example but not limited to, a USB version 2.0 for connection to a Windows XP device over a USB 2.0 cable, a composite video version for connection to a NTSC over a composite video cable, a UWB wireless video version (USB) using a USB 2.0 signal, and/or a UWB wireless video version using an NSTC signal to name a few.

In this manner, any sensitive electronics may be removed from the handle, for example, during the sterilization process so that they are not exposed to the relatively high temperatures encountered during the process.

The blade of the laryngoscope is advantageously provided with a smooth upper surface such that the physician may use the laryngoscope either in the "video mode" or in may intubate a patient by direct visualization as desired. It is further contemplated that a plurality of blades may be detachably connectable to the handle, while the enclosure is detachably connectable to the blade and/or handle.

While it is preferred to locate the digital imaging device and the LED in the enclosure that is attachable to the blade, it is contemplated that one or both of the digital imaging device and/or the LED may be positioned in the removable universal control circuit that is detachably coupled to the handle.

It is still further contemplated that the endoscopic device may be provided with a direct wired connection to, for example, a video monitor, or may be provided with a wireless connection to the display equipment, which may comprise use of Ultra Wide Band (UWB) technology.

It is yet further contemplated that the endoscopic device could comprise and endoscope including, for example, a rigid endoscope, a flexible endoscope and the like. The digital imaging device and the LED may be positioned at a distal end of the endoscope with the universal control circuit may be positioned in the handle of the endoscope. It is contemplated that the various features as described in connection with a laryngoscope are equally applicable to use in an endoscope. When the LED is positioned at a distal end of the endoscope shaft, it may be used to both illuminate the area ahead of the shaft and to defog a window enclosing the LED. In this embodiment, power may be supplied to the LED via either a battery provided at the distal end of the shaft or via an electrical channel extending from the handle to the shaft. Additionally, the imaging device may be provided adjacent to the LED to pick up reflected light from the area to be viewed and as previously discussed, by comprise either a wired or wireless connection to the control circuit. Likewise, a power source, such as a battery may either be provided at the distal end to power the imaging chip or may be remotely provided.

Accordingly, in one advantageous embodiment a laryngoscope system is provided comprising a handle having a cavity located therein, the cavity having a connector, a blade coupled to the handle and a control circuit detachably connectable to the connector. The laryngoscope system also comprises a sleeve coupled to the control circuit, an illuminating device for providing illuminating light to an area in front of the distal end of the blade and a digital imaging device for generating image data of the area in front of the distal end of the blade. In addition, the laryngoscope system includes a display coupled to the control circuit, the display receiving and displaying the image data.

In another advantageous embodiment a method for incubating a patient with a laryngoscope is provided comprising the steps of coupling a control circuit to a connector located in a cavity in a handle, coupling a blade to the handle and coupling a sleeve to the control circuit. The method includes the steps of transmitting illuminating light to an area in front of the distal end of the blade, generating image data of the area in front of the distal end of the blade and transmitting the image data to the control circuit. The method further includes the steps of coupling a display to the control circuit, transmitting the image data to the display and displaying the image data on a display.

In still another advantageous embodiment an endoscopic device is provided comprising a handle having a cavity located therein with a connector positioned in the cavity and a shaft coupled to the handle. The device further includes a control circuit detachably connectable to the connector and an illuminating device for providing illuminating light to an area in front of the distal end of the shaft. The device still further includes a digital imaging device for generating image data of the area in front of the distal end of the shaft and a display coupled to the control circuit, the display receiving and displaying the image data.

In yet another advantageous embodiment a method for operating an endoscopic device is provided comprising the steps of coupling a control circuit to a connector located in a cavity in a handle and transmitting illuminating light to an area in front of a distal end of a shaft coupled to the handle. The method further comprises the steps of generating image data of the area in front of the distal end of the blade and transmitting the image data to the control circuit. The method still further comprises the steps of coupling a display to the control circuit, transmitting the image data to the display and displaying the image data on a display.

Other objects of the invention and its particular features and advantages will become more apparent from consideration of the following drawings and accompanying detailed description.

DETAILED DESCRIPTION OF THE INVENTION

Figure 1:
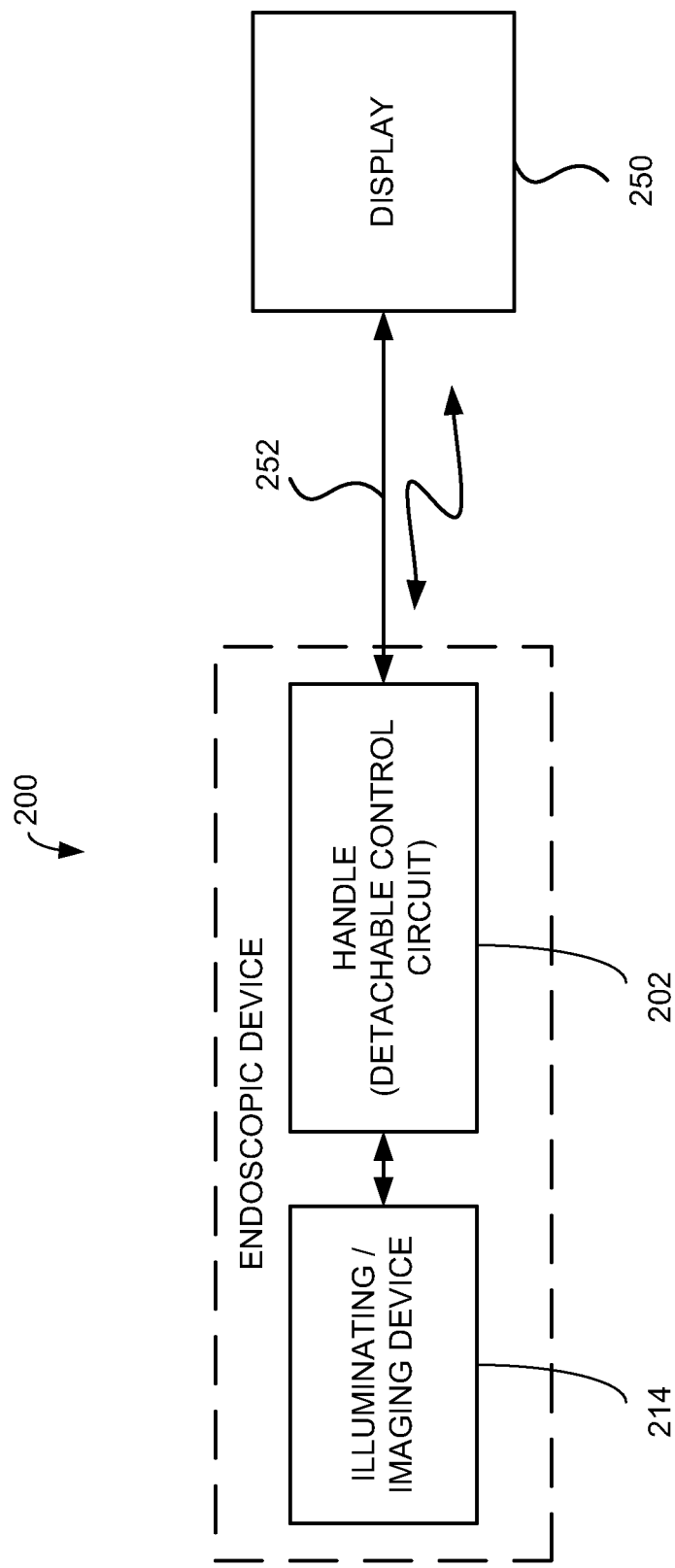
FIG. 1 is a block diagram of one advantageous embodiment of the present invention.

Referring now to the drawings, wherein like reference numerals designate corresponding structure throughout the views.

Figure 2:
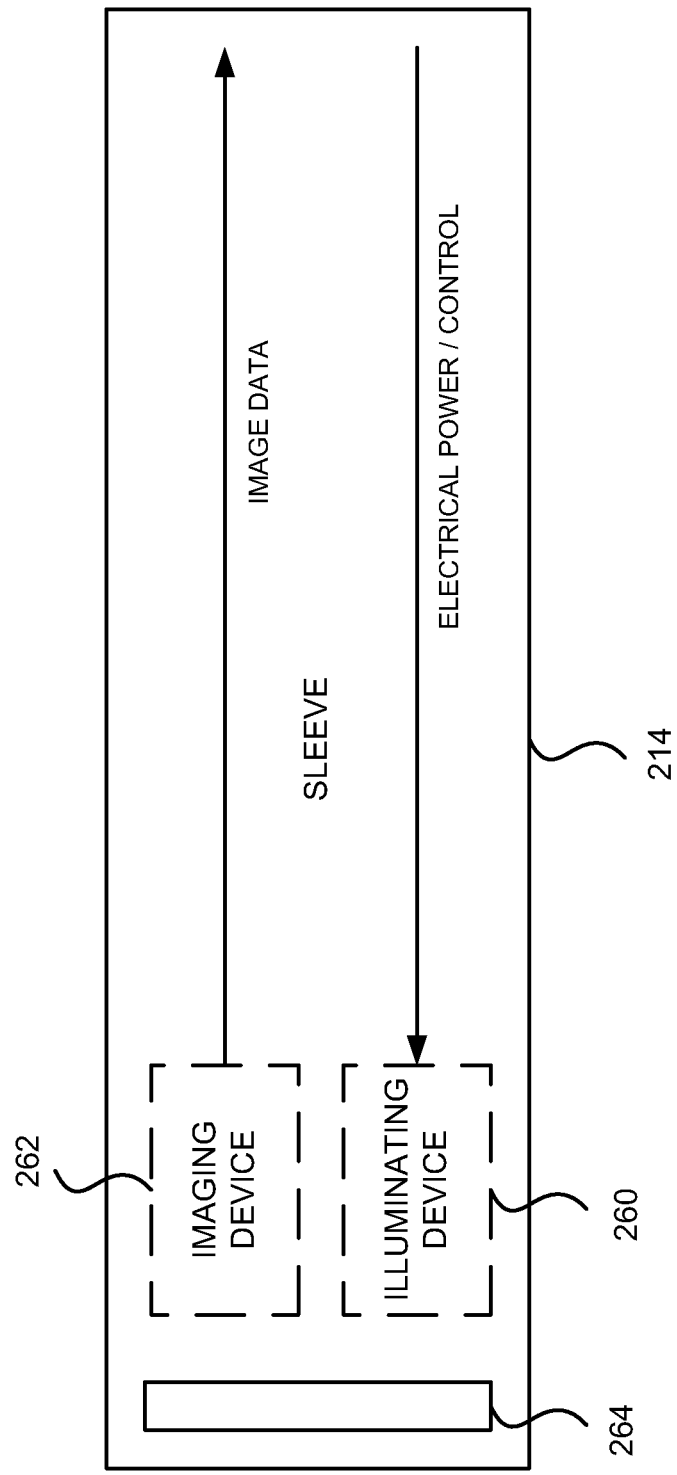
FIG. 2 is a block diagram of sleeve according to FIG. 1.

One advantageous embodiment of the present invention is variously illustrated in FIGS. 1-7 including endoscopic device 200. FIGS. 1 and 2 are block diagrams illustrating various functional arrangements of endoscopic device 200, while FIGS. 3-7 are various prospective views of an advantageous embodiment of the present invention.

Figure 1A:
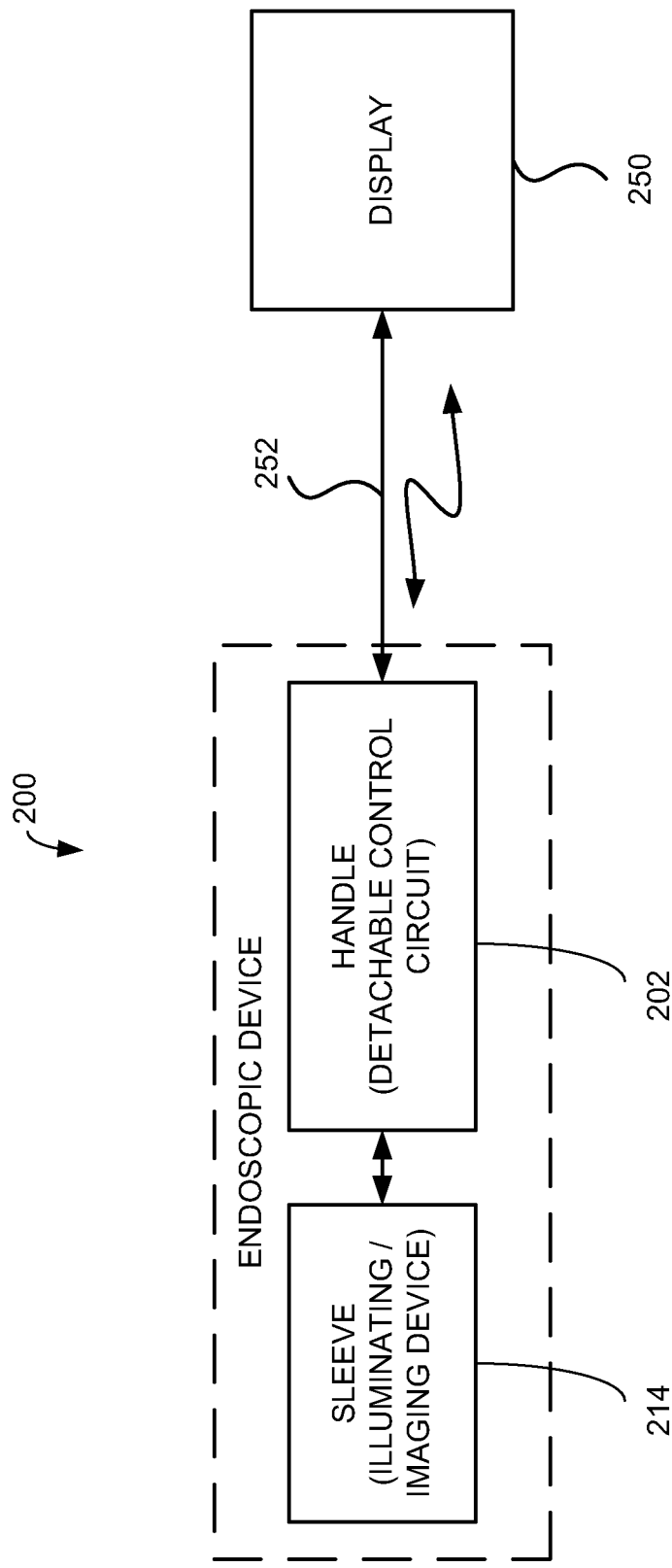
FIG. 1A is a block diagram of the embodiment according to FIG. 1.

Endoscopic device 200 generally comprises a control circuit 202, which is insertable into or detachably connectable to a handle 204 of the endoscopic device 200. In addition, when the endoscopic device comprises a laryngoscope, a blade 206 is coupled to handle 204 and an illuminating/imaging device 214 (in one embodiment including a sleeve) may be coupled to control circuit 202 for transmitting image data to the control circuit, which is in turn, transmitted to a display 250. FIGS. 1 and 1A illustrate use of, for example, a cable 252 or use of a wireless coupling to display 250. Alternatively, endoscopic device 200 may comprise an endoscope also having an illuminating/imaging device 214 coupled to a control circuit 202.

It is contemplated that cable 252 may provide electrical power to control circuit 202 and may also transmit image data to display 250. However, in a wireless embodiment, a battery may be located in handle 204

Referring to FIG. 2, an imaging device 260 and an illumination device 262 are each positioned at a distal end of endoscopic device 200. Also illustrated is window 264. Illumination device 262 may comprise, for example, an LED positioned adjacent to window 264. Illumination device 262 is provided for illumination of an area to be viewed, such as, for example, an area ahead of the distal end of endoscopic device 200. It is contemplated that illumination device 262 may operate in a fully ON state when endoscopic device 200 is in use, or may, in one advantageous embodiment, be pulsed in sync with imaging device 260. In addition, the LED may be used to de-fog window 264. In one embodiment, the LED provided as a relatively high-powered LED and run at half power or more providing both illumination and heating of the window 264 to provide a de-fogging function.

In a battery-powered version, the battery may comprise any battery type as is commonly used in industry and is contemplated that it may have a twelve-hour battery life. Further, the battery may in one advantageous embodiment be rechargeable.

Imaging device 260 may pick up reflected light from an area to be viewed and translates the reflected light into image data that is transmitted for display on display 250. This transmission may advantageously comprise a hard-wired connection or may be wireless. For hard-wired connections, the cable may comprise an electrical connection providing power to control circuit 202 and image data to display 250. It is further contemplated that data signals, control signals and power may all be transmitted over a signal channel thereby minimizing the size of the interconnecting cables.

For wireless transmission, any acceptable transmission means may be used including but not limited to, for example, radio-frequency transmission or the like. In one embodiment, transmission circuitry is positioned in handle 204 for transmission of the image data to display 250.

The coupling between endoscopic device 200 and display 250 is illustrated in FIG. 1 as either a curved line with arrows in two different directions (wireless) or the straight line with arrows in two different directions (hard-wired). Display 250 may comprise virtually any commercially available video system and monitor for display of the image data generated by imaging device 260.

In an advantageous embodiment, wireless transmission may comprise an UWB transmission. As UWB systems transmit signals across a much wider frequency than conventional systems, a relatively large amount of data may be transmitted. This is advantageous for video medical systems, where relatively high resolution is beneficial and signal lag is undesirable. A number of UWB technologies may effectively be used including, for example, Multiband Orthogonal Frequency Division Modulation (OFDM) or Direct Sequence Ultra-Wideband (DS-UWB).

It is contemplated that imaging device 260 may comprise, in one advantageous embodiment, a CMOS chip (e.g. OmniVision's OV7660 VGA CMOS sensor). The CMOS chip may be made relatively small in size, utilizes very little power and is inexpensive to manufacture and may be connected to any necessary drive electronics using a flex circuit. In addition, the signal format may be selected to utilize non-sinusoidal signals, which will not interfere with the sinewave spectrum so as to minimize any interference in existing operating room equipment. This advantage may be is achieved, at least in part because the transmitted power may be spread over a relatively large bandwidth such that the amount of power at any one frequency band at any time is relatively small.

Figure 3:
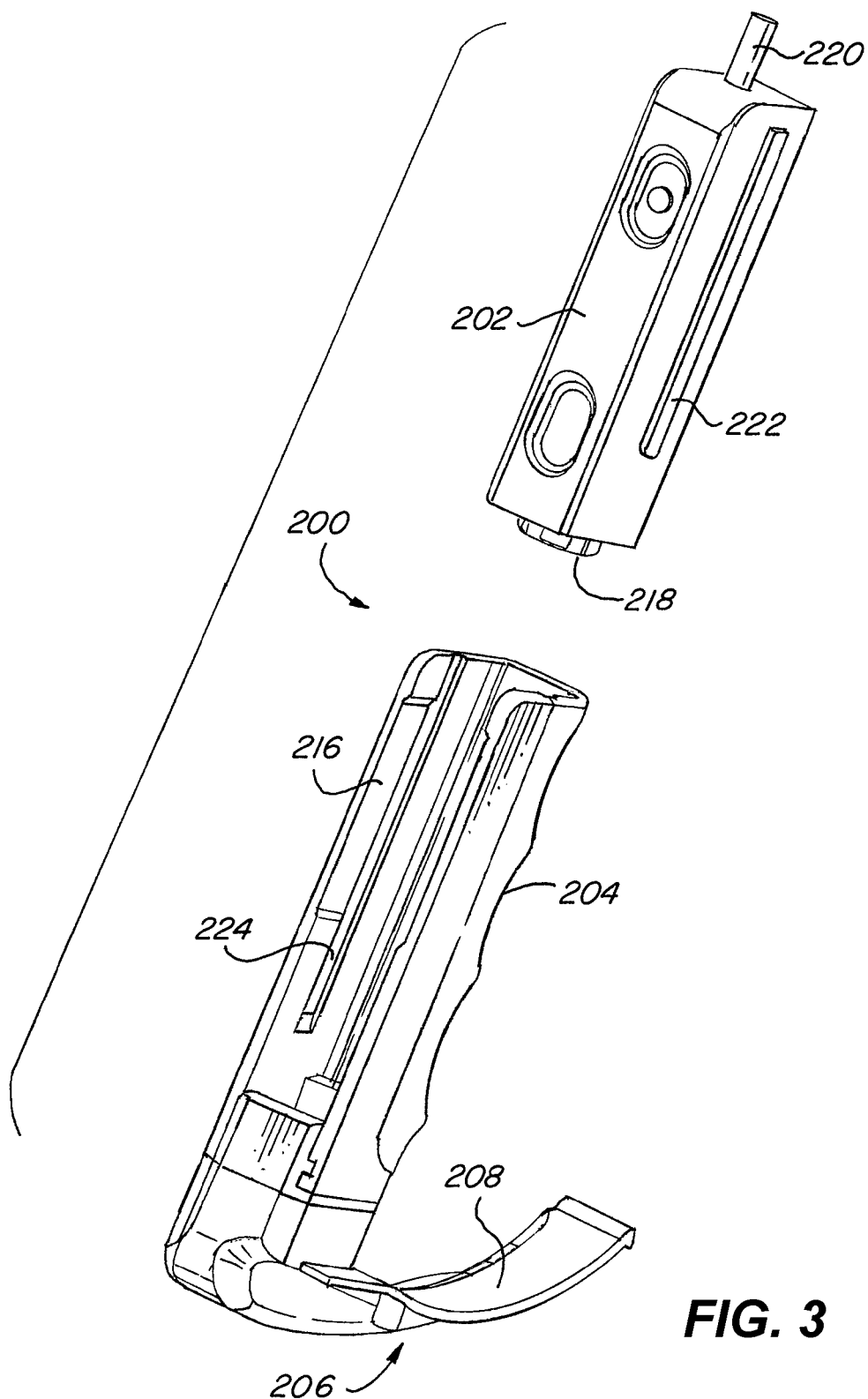
FIG. 3 is a perspective view of the embodiment according to FIG. 1.
Figure 4:
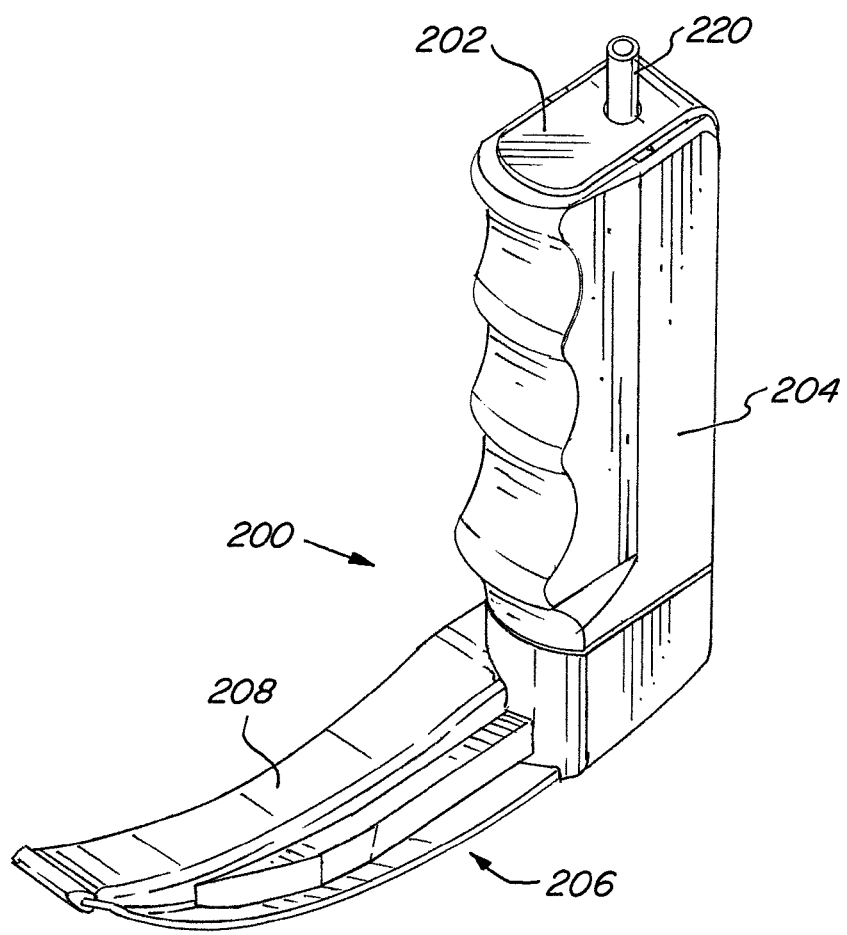
FIG. 4 is another perspective view of the embodiment according to FIG. 1.

Referring to FIG. 3, in one advantageous embodiment, blade 206 is detachably connectable to handle 204. Advantageously, blade 206 is provided slightly curved upward as a traditional Macintosh style blade, but could be provided relatively straight as per the traditional Foregger-Magill blade. As can be seen in FIG. 4, blade 206 is advantageously provided with a relatively smooth upper surface 208, which in part, allows the physician to use endoscopic device 200 either in the video mode (e.g. viewing a video screen during the intubation process) or via direct visualization. It is contemplated that in one embodiment, blade 206 may be provided as a rigid material, such as a metal or an alloy, but is not limited to these material compositions.

Figure 5:
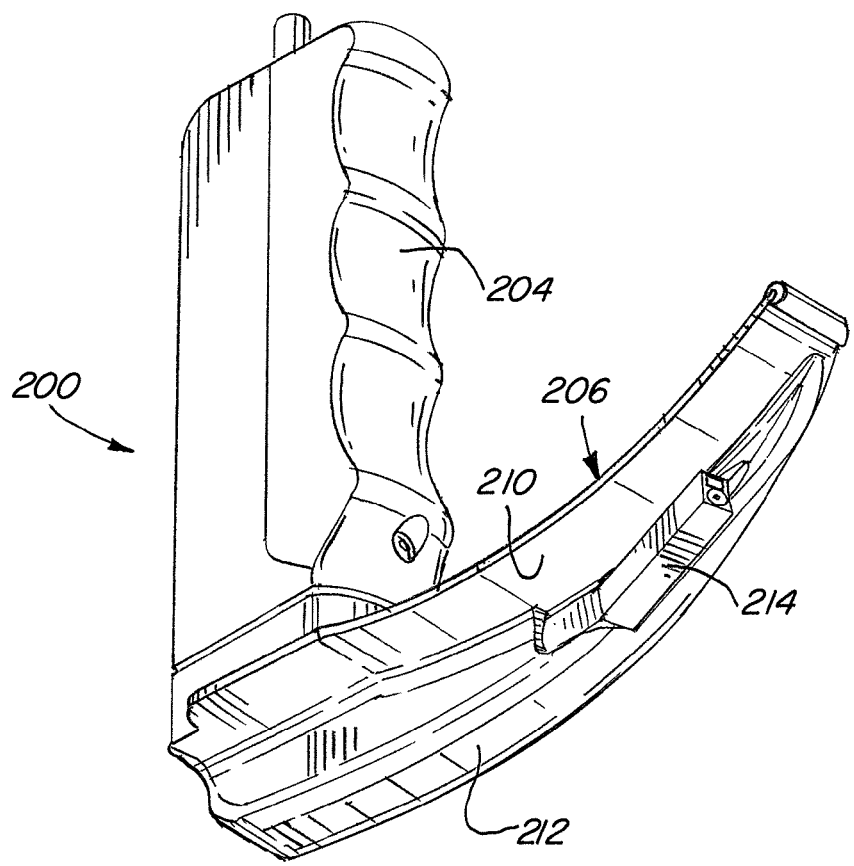
FIG. 5 is still another perspective view of the embodiment according to FIG. 1.
Figure 6:
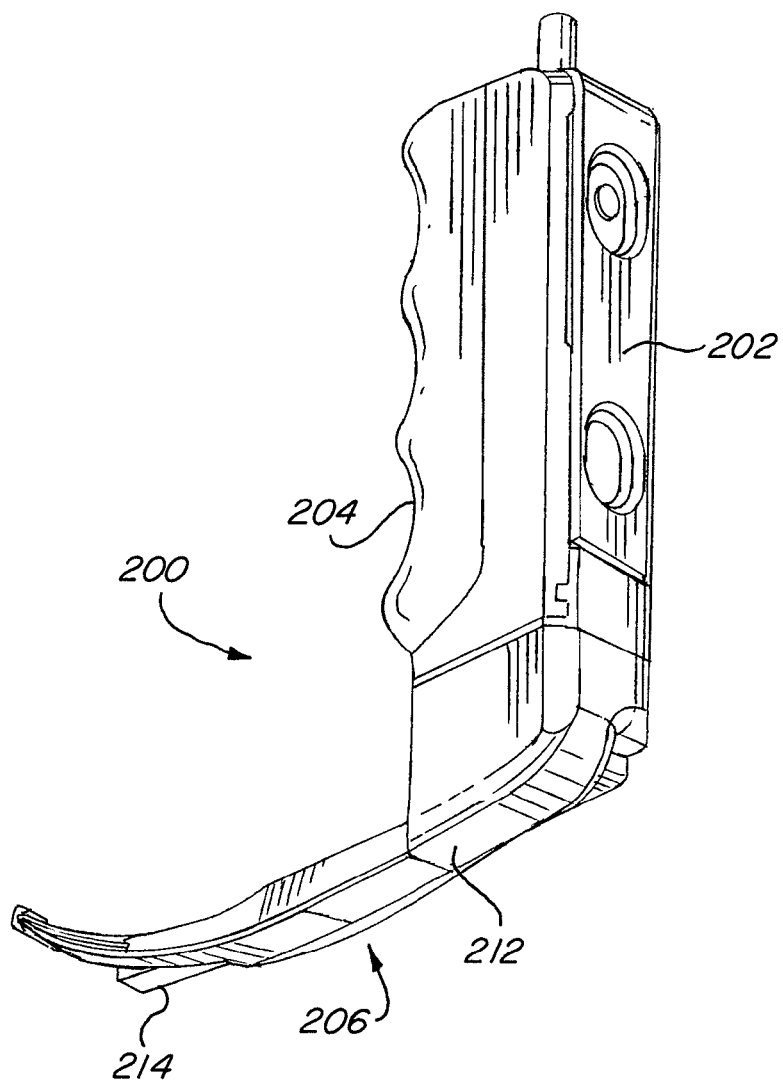
FIG. 6 is yet another perspective view of the embodiment according to FIG. 1.
Figure 7:
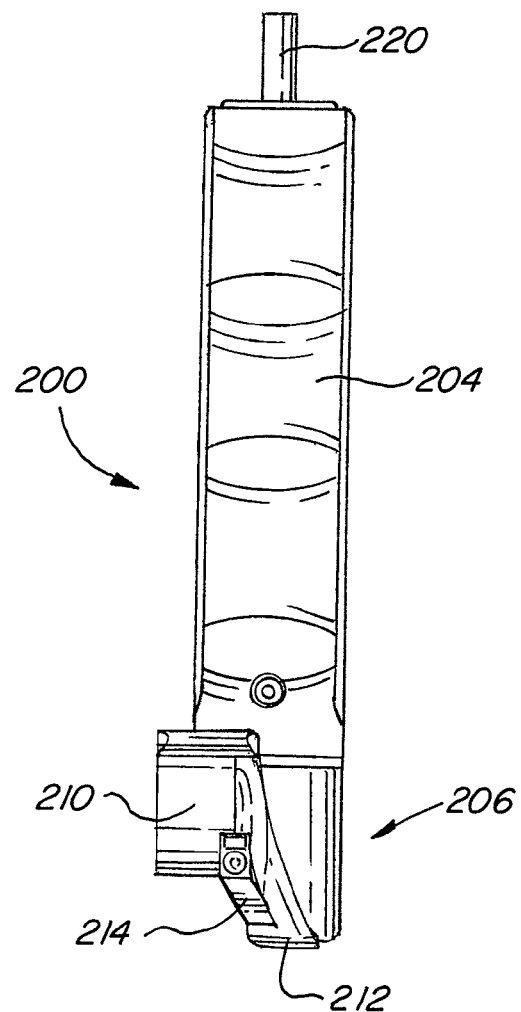
FIG. 7 is still another perspective view of the embodiment according to FIG. 1.

As seen in FIGS. 5 and 6, blade 206 is provided with a stepped portion 210 such that a cavity is formed in the lower portion 212 of blade 206 for receiving sleeve 214, which may be detachably connectable to blade 206. As in the previously described embodiments, the illumination may be provided by an LED, which in this embodiment, is positioned in sleeve 214. In addition, the imaging device may also be positioned in sleeve 214 and may comprise a digital imaging device such as a CMOS device or chip.

As seen in FIG. 1, control circuit 202 is insertable into a cavity 216 of handle 204 and lies essentially flush with handle 204 with fully inserted (FIG. 4). It is contemplated that the device may provide an audible "click" when camera 202 is fully inserted into cavity 216 providing an audible indication to the user that the coupling of control circuit 202 to handle 204 is complete. It is further contemplated that a lock, such as an interference fitting between control circuit 202 and cavity 216, may be provided to maintain control circuit 202 securely coupled to handle 204 during use. Also provided on the exterior surface of control circuit 202 is protrusion 222, which is provided as a ridge running along a longitudinal length of control circuit 202. Protrusion 222 is provided to engage with a channel 224 located in cavity 216. In this manner, the control circuit 202 may only be removed from cavity 216 by longitudinally sliding the control circuit 202 out of cavity 216.

A coupler 218 is provided at the insertion end of camera 202, which is designed to engage with a complementary connector (not shown) positioned inside cavity 216 of handle 204. Depending upon the application, the coupler may couple, electrical cables/channels, optical cables/channels and/or combinations thereof. In addition, cable 220 may be provided to channel electrical signals, optical signals/energy and/or combinations thereof between camera 202 and the video system (Display).

Figure 8:
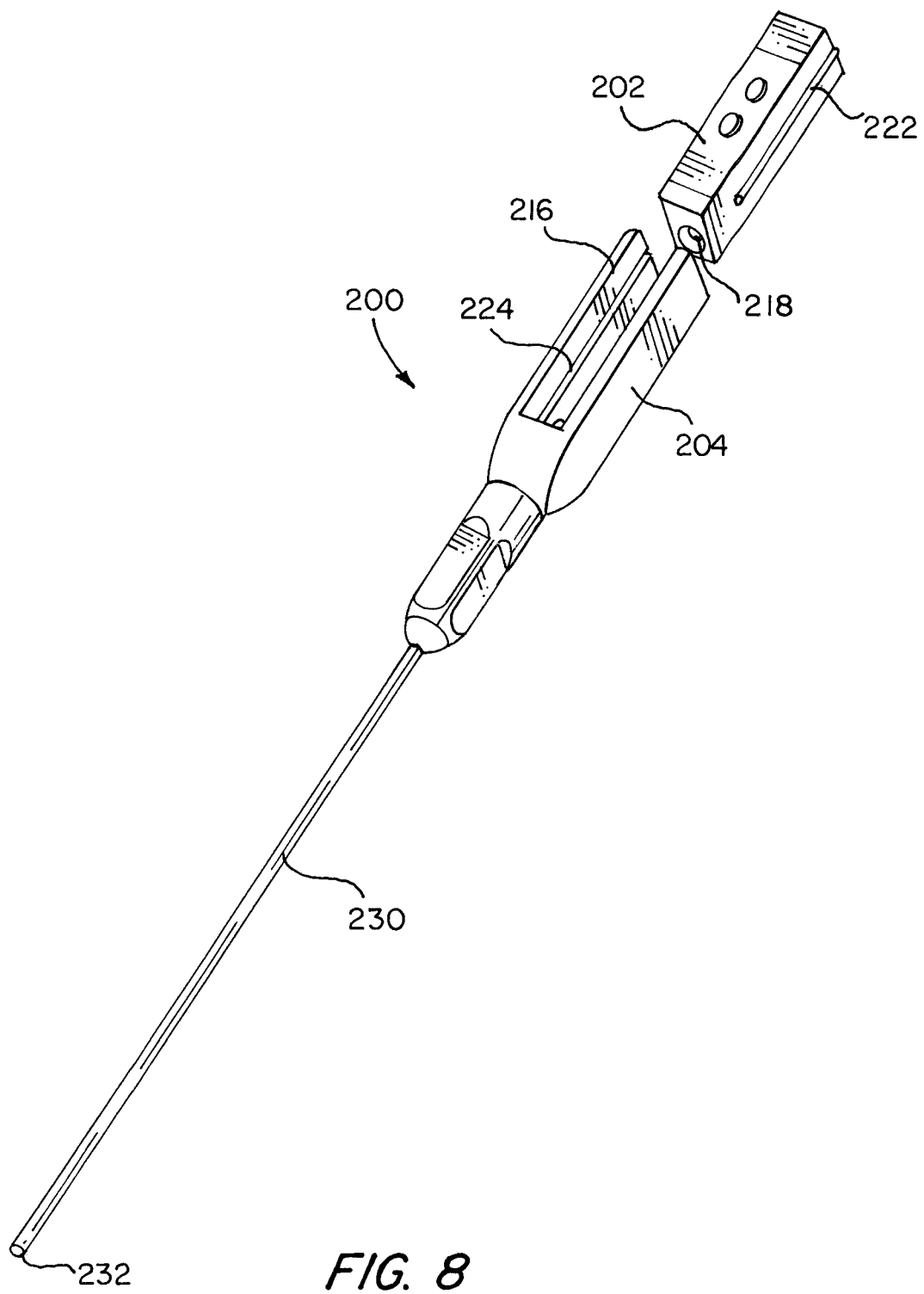
FIG. 8 is an illustration of the embodiment according to FIG. 1 where the endoscopic device comprises an endoscope having a straight rigid shaft.
Figure 9:
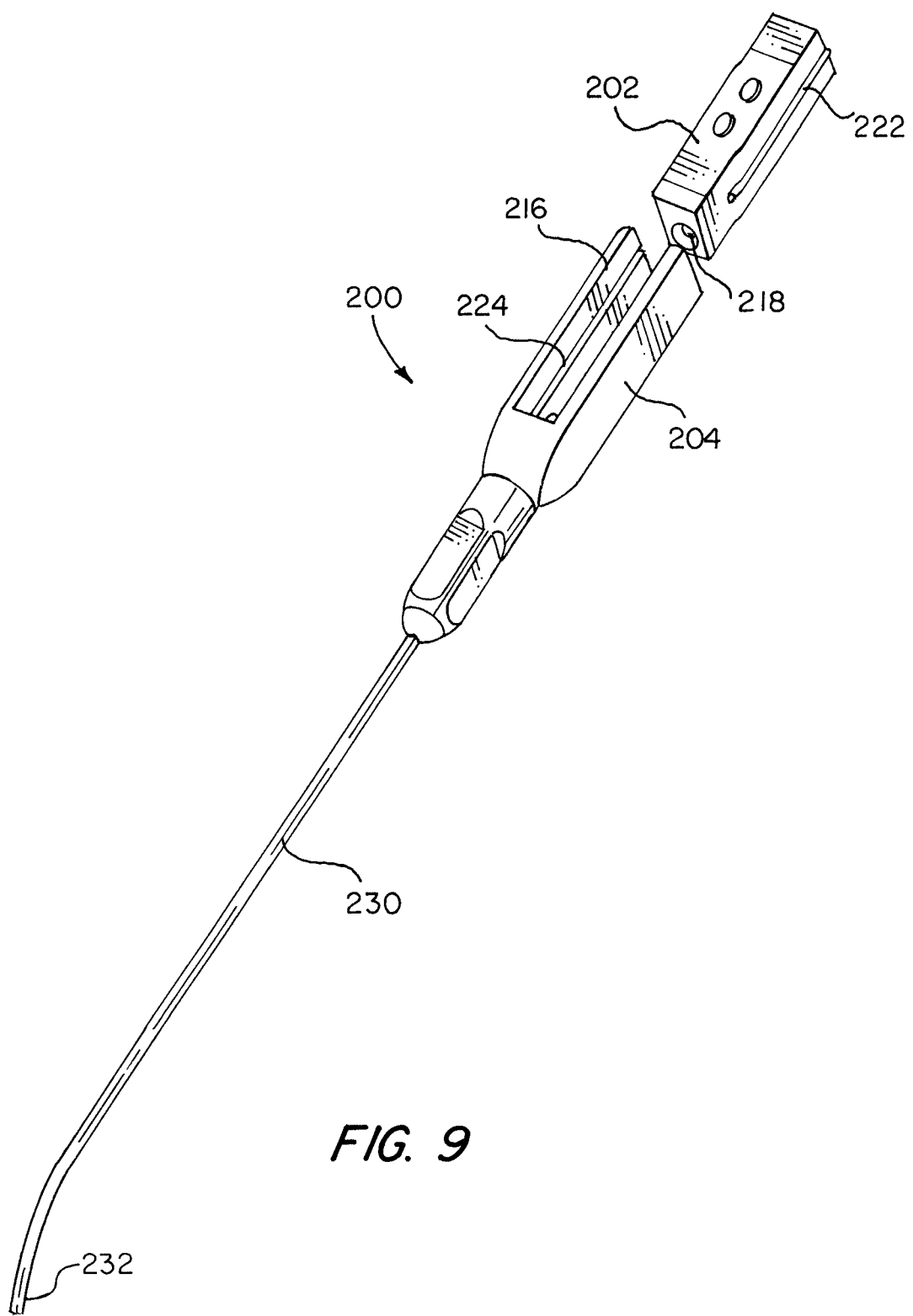
FIG. 9 is an illustration of the embodiment according to FIG. 1 where the endoscopic device comprises an endoscope having a bent rigid shaft.

Referring now to FIGS. 8-13, endoscopic device 200 comprises an endoscope. As illustrated in FIGS. 8 and 9, endoscopic device 200 can comprise in one embodiment, a rigid endoscope having a shaft 230 that is either straight or bent. It is contemplated that the shaft 230 includes a distal end 232 from which illuminating light may emit and into which reflected light can enter. As shown in FIG. 2, illuminating device 260 and imaging device 262 may be positioned at distal end 232.

Figure 10:
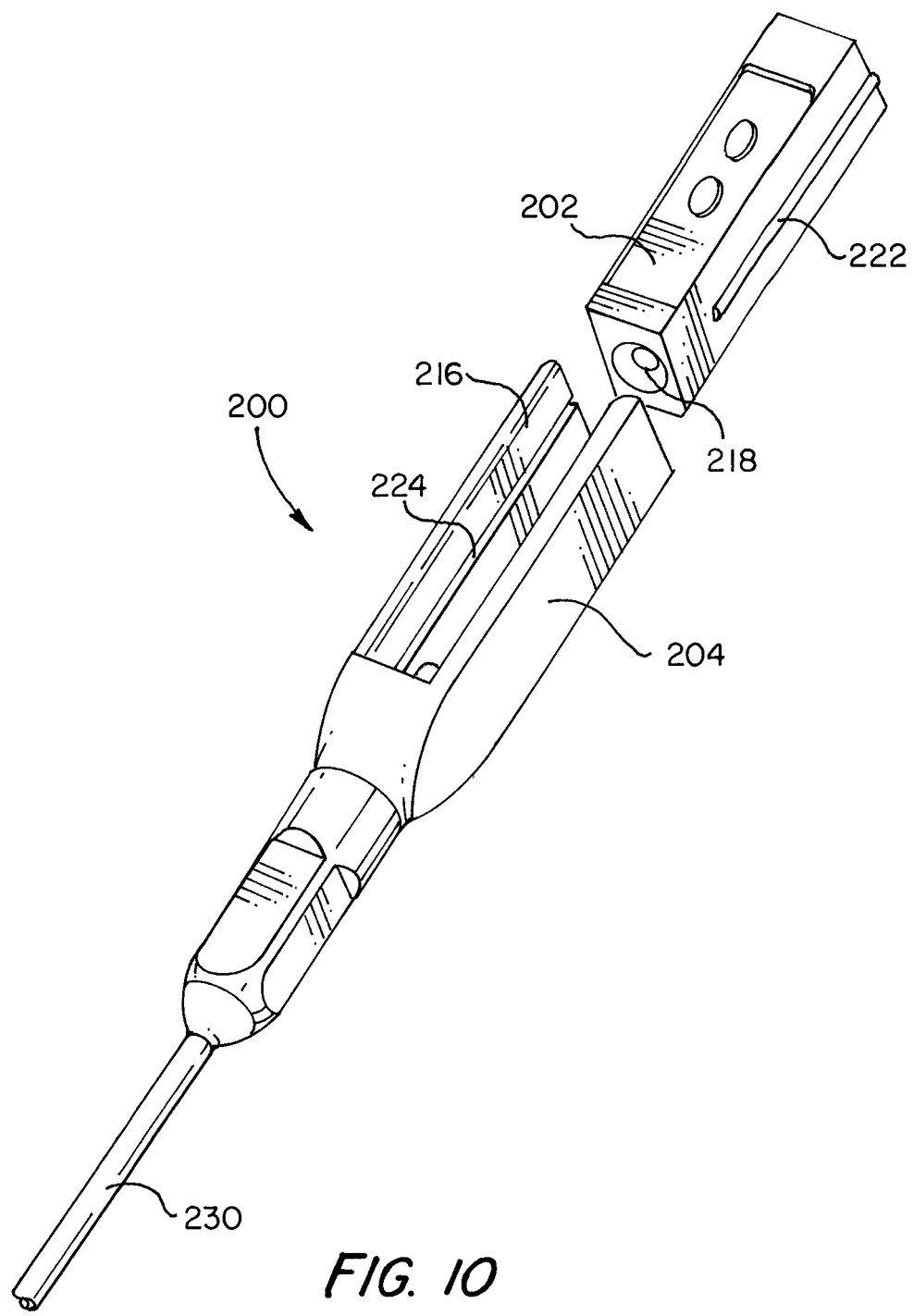
FIG. 10 is a view of the endoscopic device according to FIGS. 8 and 9.
Figure 11:
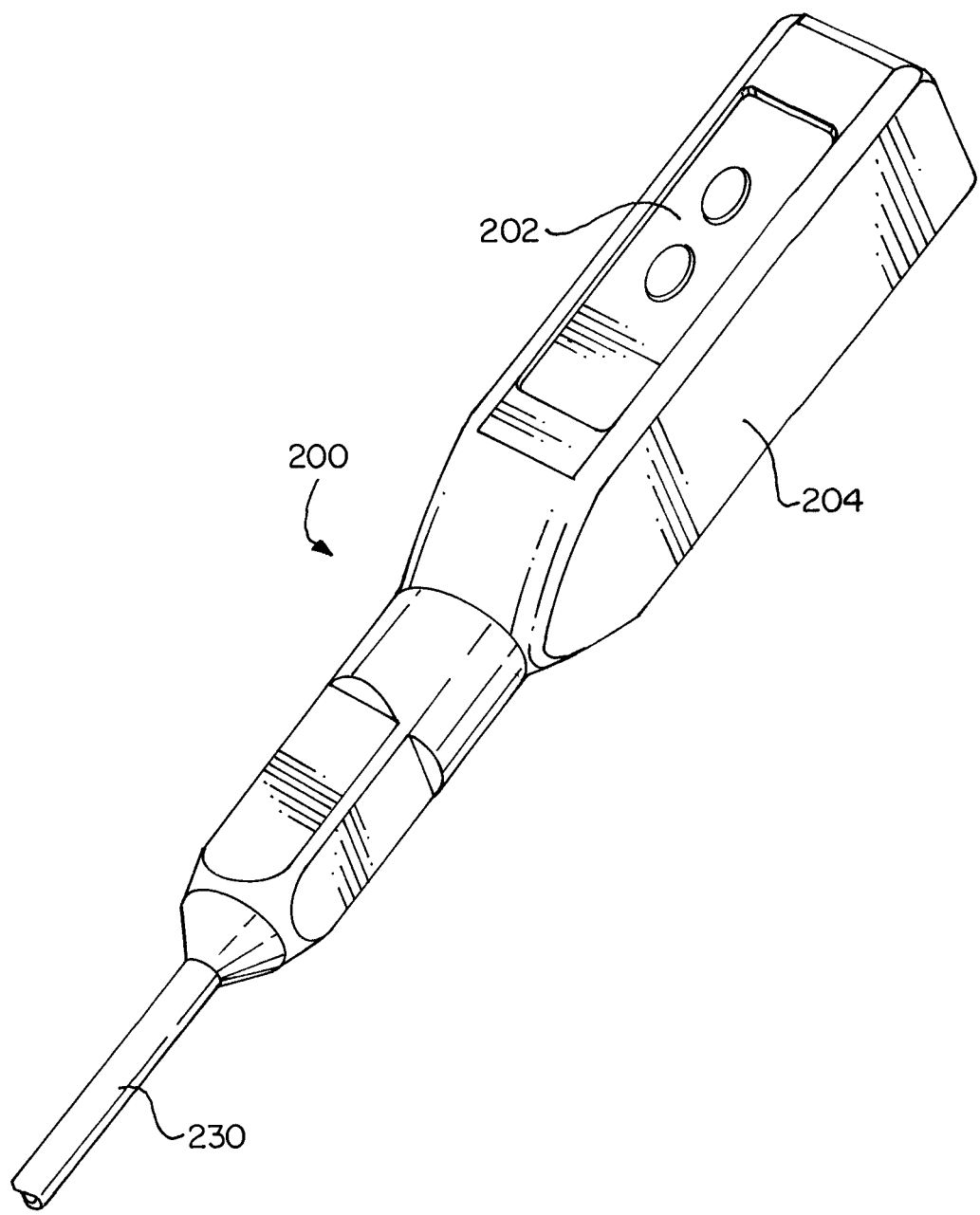
FIG. 11 is a view of the endoscopic device according to FIGS. 8 and 9.

Referring now to FIGS. 10 and 11, it can be seen that control circuit 202 is insertable into cavity 216 and lies substantially flush with handle 204 with fully inserted. As described in connection with the laryngoscope embodiment, and audible indication may be presented to the user when the control circuit 202 is fully inserted into cavity 216.

Also illustrated is protrusion 222 on the exterior surface of control circuit 202, which is provided as a ridge running along a longitudinal length of control circuit 202 and is designed to engage with a channel 224 located in cavity 216.

Figure 12:
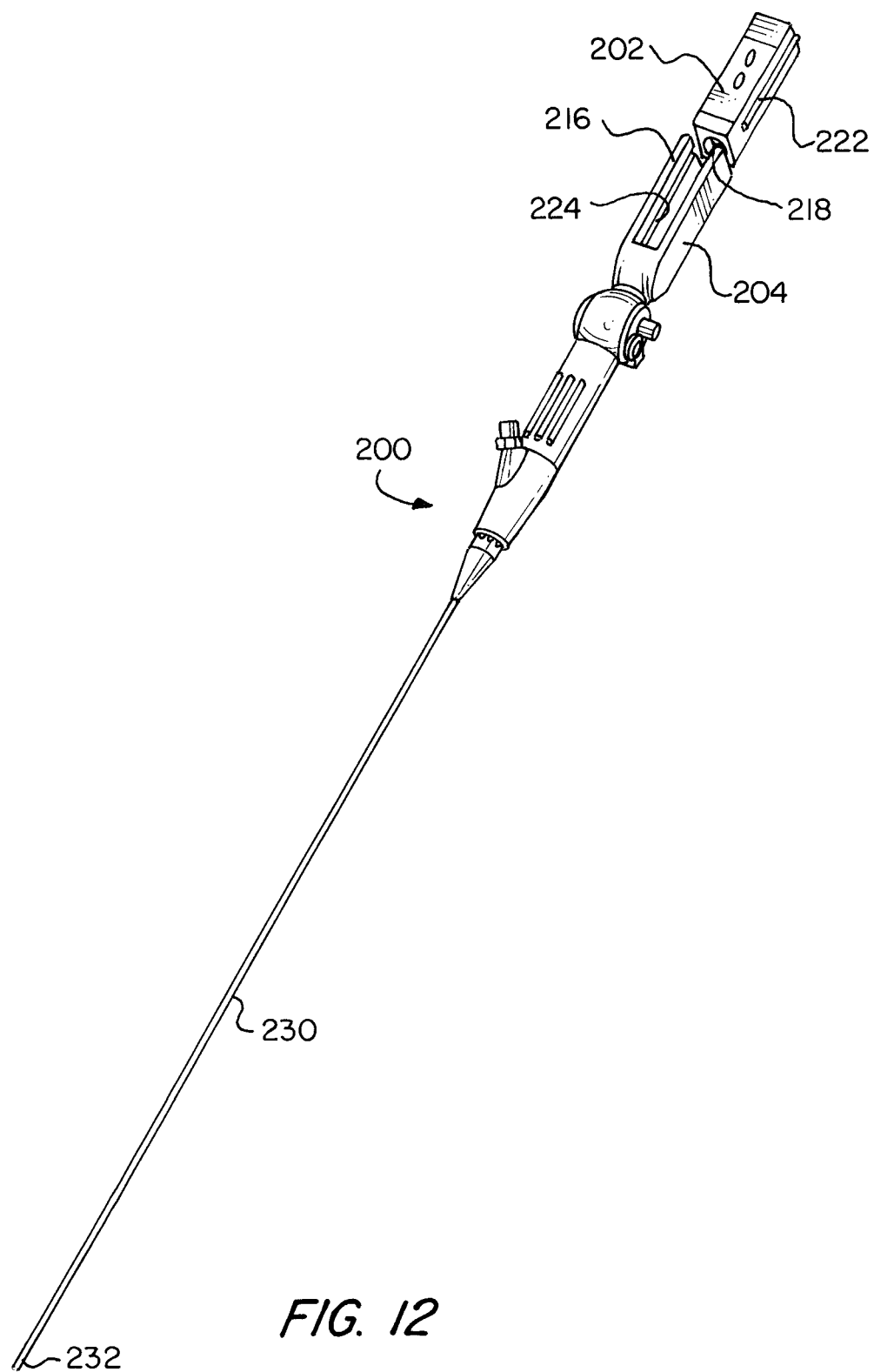
FIG. 12 is an illustration of the embodiment according to FIG. 1 where the endoscopic device comprises an endoscope having a flexible shaft.
Figure 13:
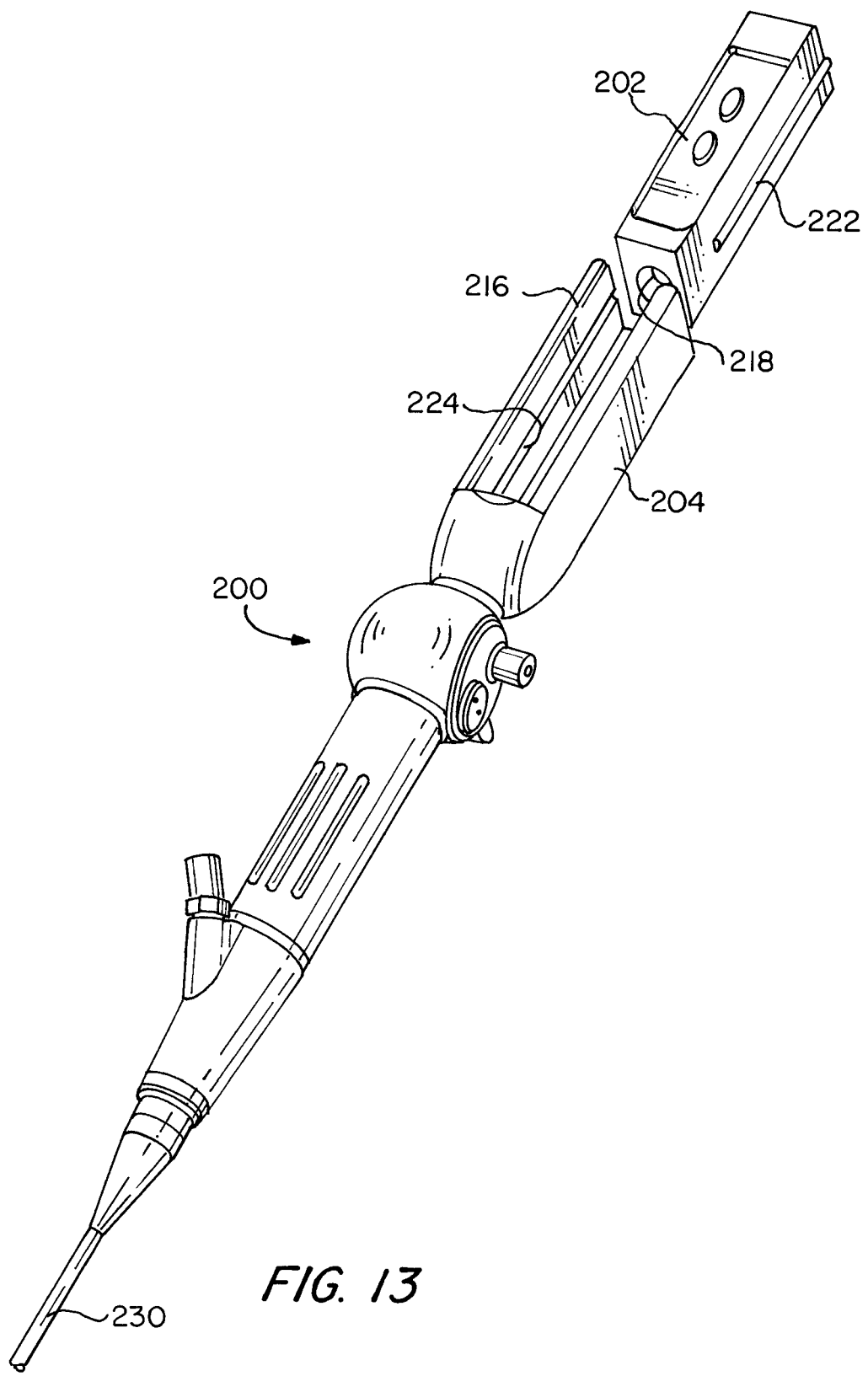
FIG. 13 is an view of the endoscopic device according to FIG. 12.

A similar embodiment is illustrated in FIGS. 12 and 13 where the control circuit 202 is illustrated as being detachably connectable with a flexible endoscope.

The configurations illustrated here show that flexibility of the current system, allowing the physician to simply remove the control circuit 202 as desired. In this manner, it is a relatively quick and easy process to change from one control circuit to another without having to replace or change the current endoscopic device 200.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscopic device comprising:
   a handle having a cavity located therein with a connector positioned in the cavity, the cavity having an elongated channel positioned therein extending longitudinally along a length of said cavity;
   a shaft coupled to said handle;
   a control circuit having a housing with an outer surface and a protrusion positioned on the outer surface and a coupler positioned at one end of the housing, the coupler being detachably connectable to the connector;
   an illuminating device generating illuminating light provided to an area in front of the distal end of said shaft, said illuminating device is positioned in said shaft;
   an imaging device generating image data corresponding to the area in front of the distal end of said shaft, said imaging device is positioned in said shaft;
   said connector having an electrical channel transmitting electrical power to said illuminating device and said imaging device and a data channel transmitting the image data generated by said imaging device;
   a display coupled to said control circuit, said display receiving and displaying the image data;
   wherein when the control circuit is inserted into and received within the cavity, the protrusion engages with the elongated channel such that as said control circuit is advanced into the cavity, the protrusion moves within said elongated channel so that the coupler aligns with and engages with the connector when said control circuit is fully inserted into the cavity.

2. The endoscopic device according to claim 1 wherein said shaft comprises a flexible portion.

3. The endoscopic device according to claim 1 further comprising a cable coupling said imaging device to said display.

4. The endoscopic device according to claim 3 wherein said cable comprises a USB cable.

5. The endoscopic device according to claim 3 wherein said cable comprises a cable carrying an NTSC signal and connector.

6. The endoscopic device according to claim 1 wherein said illuminating device comprises an LED.

7. The endoscopic device according to claim 6 wherein the LED is pulsed in sync with a shutter of said imaging device.

8. The endoscopic device according to claim 6 further comprising a window positioned at a distal end of said shaft and said LED is positioned adjacent to said window to heat and defog the window.

9. The endoscopic device according to claim 1 wherein upon connection to a display, said control circuit identifies said connected display and provides an image data stream compatible with the connected display.

10. The endoscopic device according to claim 1 wherein when said coupler engages with said connector, there is an audible indication that the control circuit is fully inserted into said cavity.

11. A method for operating an endoscopic device comprising the steps of:
    providing a control circuit with a housing having an outer surface with a protrusion positioned thereon and a coupler positioned at one end of the housing;
    providing a handle with a cavity located therein with a connector positioned in the cavity, the cavity having an elongated channel positioned therein extending longitudinally along a length of said cavity;
    providing a shaft coupled to the handle;
    positioning an illumination device and an imaging device in the shaft;
    inserting the control circuit into the cavity such that as said control circuit is advanced into the cavity the protrusion engages with and moves within the elongated channel to align the coupler with the connector;
    engaging the coupler with the connector when said control circuit is fully advanced into the cavity such that the control circuit is coupled to the handle;
    transmitting electrical power to the illumination device and the imaging device via an electrical channel in the connector;
    generating illuminating light with the illumination device;
    transmitting illuminating light to an area in front of a distal end of the shaft;
    generating image data with the imaging device of the area in front of the distal end of the shaft;
    transmitting the image data to the control circuit via a data channel in the connector;
    coupling a display to the control circuit;
    transmitting the image data to the display; and
    displaying the image data on a display.

12. The method according to claim 11 wherein the illumination device is pulsed in sync with a shutter of the imaging device.

13. The method according to claim 11 further comprising the step of identifying connected display and providing an image data stream compatible with the connected display.

14. The method according to claim 11 further comprising the step of generating an audible sound when the control circuit is coupled to the connector.

15. The endoscopic device according to claim 1 further comprising a battery providing electrical energy to said imaging device.

16. The endoscopic device according to claim 15 wherein said battery comprises a rechargeable battery.

17. The endoscopic device according to claim 1 wherein said control circuit is coupled to said display via a wireless coupling arrangement.

18. The endoscopic device according to claim 17 wherein said wireless coupling arrangement is an Ultra-Wide Band transmission format selected from the group consisting of: Multiband Orthogonal Frequency Division Modulation (OFDM) and Direct Sequence Ultra-Wideband (DS-UWB).

19. The endoscopic device according to claim 1 wherein said imaging device is selected from the group consisting of: a CCD sensor, a CMOS sensor and combinations thereof.

20. The endoscopic device according to claim 1 wherein said imaging device comprises a digital imaging device.

21. The endoscopic device according to claim 1 wherein said protrusion comprises a ridge running along a longitudinal length of said control circuit.

22. The method according to claim 11 wherein the control circuit is coupled to the display via a wireless coupling arrangement.

23. The method according to claim 21 wherein the wireless coupling arrangement is an Ultra-Wide Band transmission format selected from the group consisting of: Multiband Orthogonal Frequency Division Modulation (OFDM) and Direct Sequence Ultra-Wideband (DS-UWB).

* * * * *